United States Patent [19]
Skiba

[11] Patent Number: 5,464,425
[45] Date of Patent: Nov. 7, 1995

[54] MEDULLARY SUTURE ANCHOR

[75] Inventor: Jeffry B. Skiba, Phoenix, Ariz.

[73] Assignee: Orthopaedic Biosystems, Ltd., Scottsdale, Ariz.

[21] Appl. No.: 200,162

[22] Filed: Feb. 23, 1994

[51] Int. Cl.⁶ .................................................. A61B 17/00
[52] U.S. Cl. ............................................ 606/232; 606/62
[58] Field of Search ............................. 606/62, 232, 72; 24/115 R, 129 R, 127, 1

[56] References Cited

U.S. PATENT DOCUMENTS

| | | |
|---|---|---|
| 2,846,712 | 8/1958 | Markman . |
| 2,913,042 | 11/1959 | Taylor . |
| 4,471,513 | 9/1984 | Ogawa ................................. 24/115 R |
| 4,590,928 | 5/1986 | Hunt . |
| 4,705,032 | 11/1987 | Keller . |
| 4,741,330 | 5/1988 | Hayhurst . |
| 5,116,226 | 5/1992 | Linkow ................................. 433/176 |
| 5,123,914 | 6/1992 | Cope .................................... 606/232 |
| 5,156,616 | 10/1992 | Meadows ............................. 606/232 |
| 5,165,892 | 11/1992 | Linkow ................................. 433/176 |
| 5,203,787 | 4/1993 | Noblitt et al. ....................... 606/232 |
| 5,236,445 | 8/1993 | Hayhurst .............................. 606/232 |
| 5,269,809 | 12/1993 | Hayhurst et al. .................... 606/232 |
| 5,356,413 | 10/1994 | Martins et al. ...................... 606/232 |

Primary Examiner—Tamara L. Graysay
Attorney, Agent, or Firm—Snell & Wilmer; Michael K. Kelly

[57] ABSTRACT

A medullary suture anchor including an elongated body having flat, angled end portions. A central bore extends through the body transverse to and centered on the longitudinal axis of the anchor. The anchor further includes channels extending along the sides of the body, such that a suture journaled through the central bore may be received within the longitudinal grooves during insertion of the anchor into a medullary canal.

20 Claims, 3 Drawing Sheets

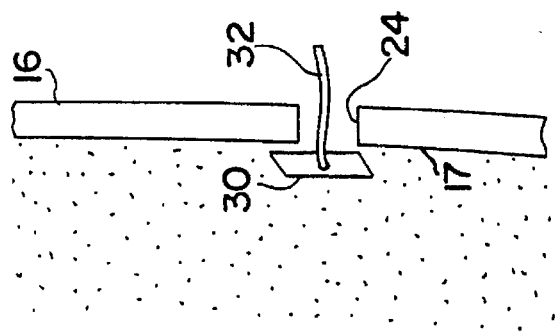
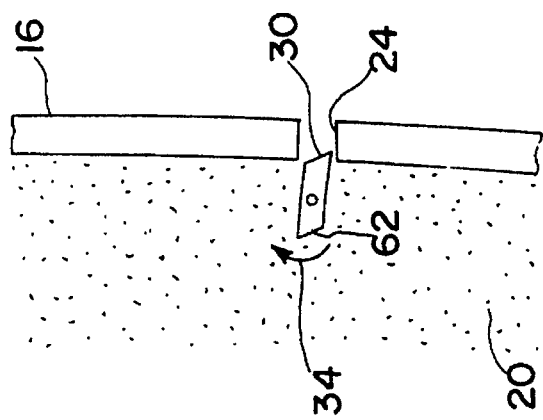
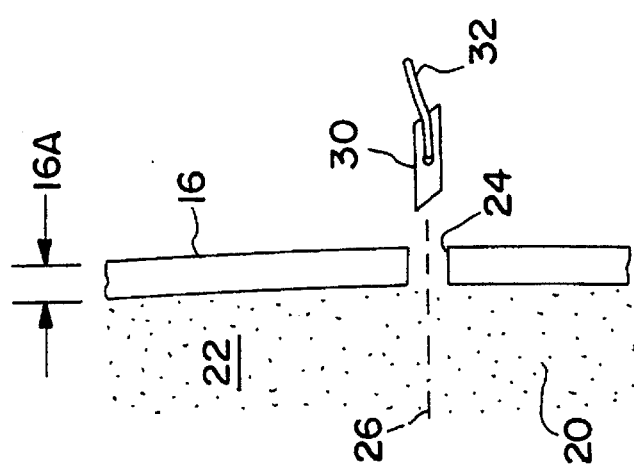

MEDULLARY SUTURE ANCHOR

TECHNICAL FIELD

The present invention relates, generally, to methods and apparatus for reattaching soft tissue to bone, and, more particularly, to a device configured for insertion through a bore into the medullary space of a bone for anchoring a suture to the bone.

BACKGROUND ART AND TECHNICAL PROBLEMS

The principal components of a skeletal system, for example a human skeletal system, include bones which comprise the framework for the body, cartilage which forms the connecting and supportive structures among the bones, and ligaments which bind the bones together. When a ligament becomes detached from a bone, for example due to an athletic or other injury, it is often desirable to reattach the ligament to the bone.

A number of techniques have been developed for reattaching soft tissue to a bone. Many of these techniques involve grasping the soft tissue to be reattached and maintaining it in intimate contact with the bone, thereby facilitating the natural physiological process whereby the soft tissue grows back into the bone to which the soft tissue is held in intimate contact. In this regard, the soft tissue may be grasped by one or more sutures, with the sutures being secured to the bone by a bone anchor device. The particular type of bone anchor device used to secure the sutures to the bone depends upon, inter alia, the physical characteristics of the bone at the reattachment site.

Those skilled in the art will appreciate that the structure of bone is generally characterized as either compact (i.e., the hard, dense, outside or "cortical" layer of bone), or spongy (also referred to herein as cancellous bone), which contains many small cavities which may be devoid of matter, or which may be filled with matter, e.g., marrow. Moreover, bones are also generally classified according to their shape; that is, bones are either long (as in the bones of the extremities), short (for example, bones of the wrist, ankle, and sesamoid bones), or flat (such as bones of the cranium, scapula, and ribs). In addition, certain bones, for example bones of the vertebrae, are classified as irregular.

A suture anchor device which is particularly useful in the context of flat bones is described in copending U.S. application Ser. No. 08/200,163 entitled "Methods And Apparatus For Attaching Soft Tissue To Bone". Anchor devices suitable for use with flat bones often employ a shaft portion configured to engage the cancellous bone, to thereby impede migration of the device in vivo. A head portion may be connected to the shaft portion of the device, the head portion being configured to accommodate one or more sutures. Anchoring the suture to the surface of a flat bone in this manner permits the sutures to maintain the soft tissue in intimate contact with the bone proximate the reattachment site.

The use of the aforementioned anchor devices in the context of long bones has been problematic for several reasons. For example, many long bones are devoid of the dense cancellous bone, thereby making it difficult for the shaft portion to engage anatomical matter underneath the bone surface. Moreover, the convex configuration of a typical reattachment site on a long bone often makes it difficult to use a conventional head as a suture attachment site.

Noblitt et al. U.S. Pat. No. 5,203,787 issued Apr. 20, 1993, discloses an anchor device comprising a relatively rigid elongate body having first and second ends and a central portion between the ends, the central portion including a site for attaching a suture thereto. The elongate body has a longitudinal axis associated therewith which extends through the first and second ends. The suture is attached to the central portion of the body at a point which is offset from the longitudinal axis. Thus, when the device is placed in a hole in the bone and a force having a component acting in a direction parallel to the longitudinal axis is applied to the suture, the device rotates causing the ends of the elongate body to engage the bone and prevent removal of the device and suture from the hole.

Other known devices attempt to dispose the suture anchor wholly within or underneath the bone surface, such as the "Quick Anchor"™ bone anchor manufactured by Mitek Surgical Products, Inc. of Norwood, Mass. The Mitek Quick Anchor bone anchor includes resiliently expandable wings extending from the body of the device. The device is configured to be inserted into a bore within a bone mass using a sleeve or collar to retain the expandable wings in a retracted position during insertion. Once the device is inserted into the bore, the wings expand such that the effective size of the device exceeds the diameter of the bore. When tension is applied to the suture, the expanded wings engage the undersurface of the bone proximate the bore, much like a grappling hook.

Known suture anchor devices are unsatisfactory in several respects. For example, the aforementioned Noblitt et al. device, with its suture attachment site offset from its longitudinal axis, requires that the device be inserted into the bore in a predetermined end-to-end orientation to permit the device to properly rotate within the bone when tension is applied to the suture. Moreover, the Noblitt et al. device necessarily requires that the diameter of the bore through which the device is inserted be greater than the effective cross-sectional area of the device to permit the sutures to be inserted through the bore simultaneously with the device. The aforementioned Mitek "Quick Anchor" is similarly unsatisfactory in that, inter alia, it requires cumbersome tools and accessories for inserting the device.

Moreover, many prior art devices exhibit complex geometrical shapes which are both difficult and expensive to manufacture and which impede the natural encapsulation process in vivo, thereby increasing the risk that the device may migrate within the bone structure.

SUMMARY OF THE INVENTION

The present invention provides an medullary anchor which overcomes the shortcomings associated with the prior art.

In accordance with one aspect of the present invention, a bone anchor comprises an elongated member having respective oppositely disposed end portions each exhibiting a terminal face disposed at a predetermined angle with respect to the longitudinal axis of the elongated member. A hole is disposed through the elongated member, for example midway between the two ends and centered on the longitudinal axis of the device. The hole is suitably sized to permit one or more sutures to be journaled therethrough.

In accordance with a further aspect of the present invention, the device suitably exhibits a cross-sectional geometry which permits the sutures to extend along at least a portion of the length of the device during insertion into a bone without increasing the effective cross-sectional area of the anchor/suture combination.

In accordance with a still further aspect of the invention, the hole through which the sutures are attached to the device is suitably beveled or radiused to avoid sharp corners which may tend to cut through the sutures.

In accordance with a still further aspect of the invention, the anchor device of the present invention may be inserted into an medullary canal in accordance with the following method: a bore is drilled through the compact bone layer and into the medullary canal. The diameter of the bore is suitably slightly greater than the largest cross-sectional dimension of the device. As the anchor is inserted into the bore, the angled face of the leading end of the device is urged against the marrow and/or other anatomical matter underneath the compact bone surface, thereby tending to rotate the anchor about an axis perpendicular to its longitudinal axis. When the device is fully inserted into the bore, the rotational action tends to urge the device into an orientation which is at an angle with respect to the bore axis. By applying tension to the sutures extending out from the bore, the anchor is further rotated until its longitudinal axis is essentially perpendicular to the bore axis. In this position, the anchor device is essentially locked underneath the bone surface proximate the bore.

In accordance with a still further aspect of the invention, serrations or other surface augmentation may be incorporated along at least a portion of the length of the device to facilitate frictional engagement of the device to the undersurface of the compact bone to which the device is anchored.

In accordance with yet a further aspect of the invention, the anchor device may be made from a bioabsorbable material such that once the soft tissue is reattached to the bone and the sutures have dissolved, the device itself may also dissolve in vivo to prevent migration of the device.

BRIEF DESCRIPTION OF THE DRAWING FIGURES

The subject invention will hereinafter be described in conjunction with the appended drawing figures, wherein like numerals designate like elements, and:

FIG. 2A is a schematic cross-section view of an exemplary soft tissue attachment site prepared for insertion of the anchor device of the present invention;

FIG. 2B shows the suture anchor substantially inserted into the bore of an exemplary suture attachment site, showing the device slightly rotated within the medullary canal;

FIG. 2C shows the suture anchor of FIGS. 2A and 2B fully inserted within the medullary canal and engaging the under-surface of the compact bone proximate the suture attachment site;

DETAILED DESCRIPTION OF PREFERRED EXEMPLARY EMBODIMENTS

Figure 1:
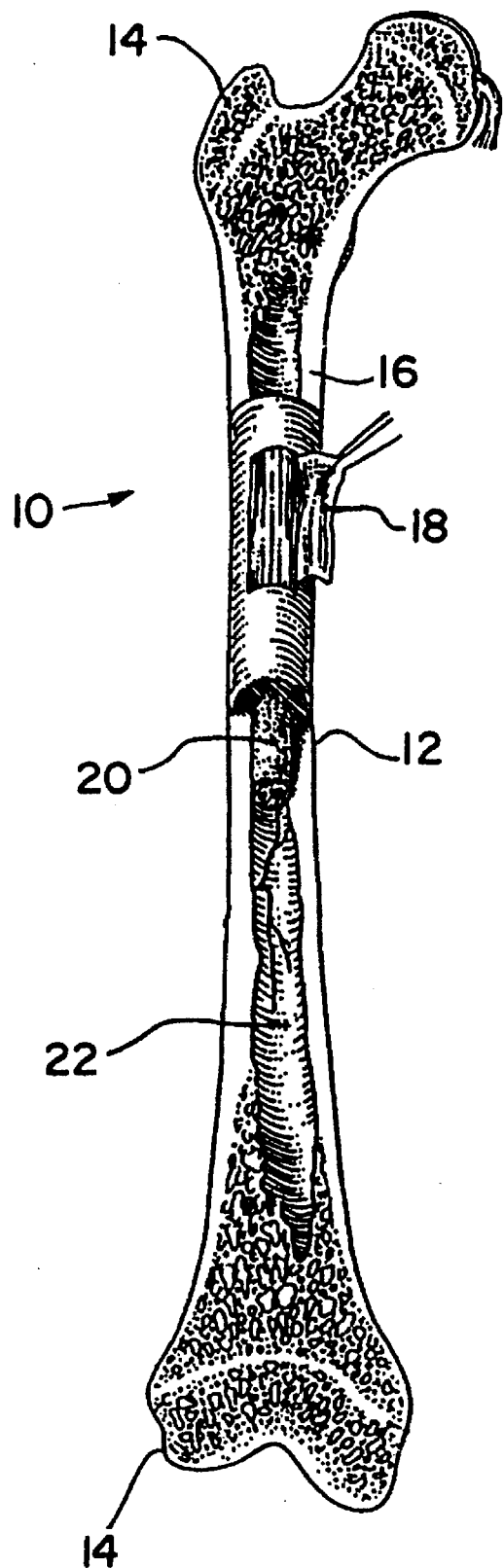
FIG. 1 is a schematic cutaway view of an exemplary long bone.

Referring now to FIG. 1, a typical long bone 10, for example a thigh bone (femur), suitably comprises a diaphysis 12 corresponding to the shaft or main central portion of a long bone, respective epiphysis portions 14 corresponding to the ends of the long bone and comprising spongy (cancellous) bone covered with a thin layer of compact bone 16, a medullary (or marrow) cavity 22 extending substantially the length of diaphysis 12 and containing marrow 20, and a periosteum 18 comprising a membrane covering compact bone 16.

When it is desired to reattach soft tissue which has become detached from the bone, for example due to an athletic or other injury, the surgeon typically prepares a reattachment site as described more fully in conjunction with FIG. 2.

Referring now to FIG. 2, a reattachment site may be suitably prepared by drilling a bore 24 through compact bone 16 and into medullary canal 22 proximate the site at which it is desired to reattach soft tissue to the bone. Bore 24 is suitably drilled with a conventional bone drill (not shown), as is known in the art.

Bore 24 has associated therewith a bore axis 26 which, although illustrated in FIG. 2 as being substantially orthogonal to the longitudinal axis of the bone, may be disposed at any desired angle with respect to the surface of the bone at the reattachment site. Depending on the density of the matter 20 (e.g., marrow) underneath the surface of compact bone 16, bore 24 may be drilled to a depth corresponding to the thickness 16A of compact bone 16; alternatively, bore 24 may extend into matter 20, for example if it is anticipated that matter 20 will pose substantial resistance as the bone anchor is inserted into the bore. Moreover, anchor 30 is well suited for use with bones in which the medullary space is substantially devoid of matter.

With continued reference to FIG. 2A, an exemplary medullary anchor 30, having one or more sutures 32 attached thereto, may be conveniently positioned for insertion into bore 24.

Referring now to FIG. 2B, device 30 may be conveniently inserted into bore 24, for example, by urging the device into the bore by thumb or finger pressure. As device 30 is inserted into the bore, an angled face 62 of the device is urged against matter 20, tending to rotate device 30 generally in the direction of arrow 34.

Referring now to FIG. 2C, once device 30 is fully inserted through bore 24 such that the entire device clears undersurface 17 of compact bone 16 (i.e., to the left in FIG. 2C), the physician applies tension to sutures 32, to thereby wedge device 30 against undersurface 17 of bone 16, thereby locking the device in place.

Figure 3B:
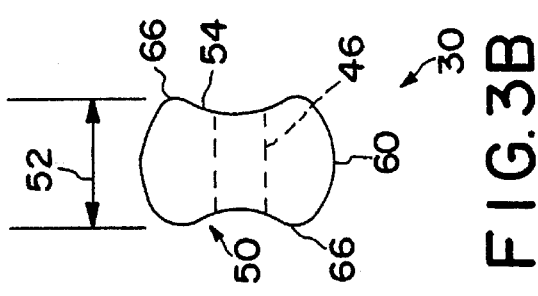
FIG. 3B is an end view of the suture anchor of FIG. 3A.
Figure 3C:
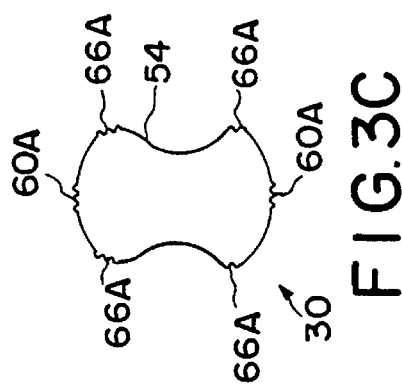
FIG. 3C is an end view of an alternative embodiment of the suture anchor of 3A.
Figure 3A:
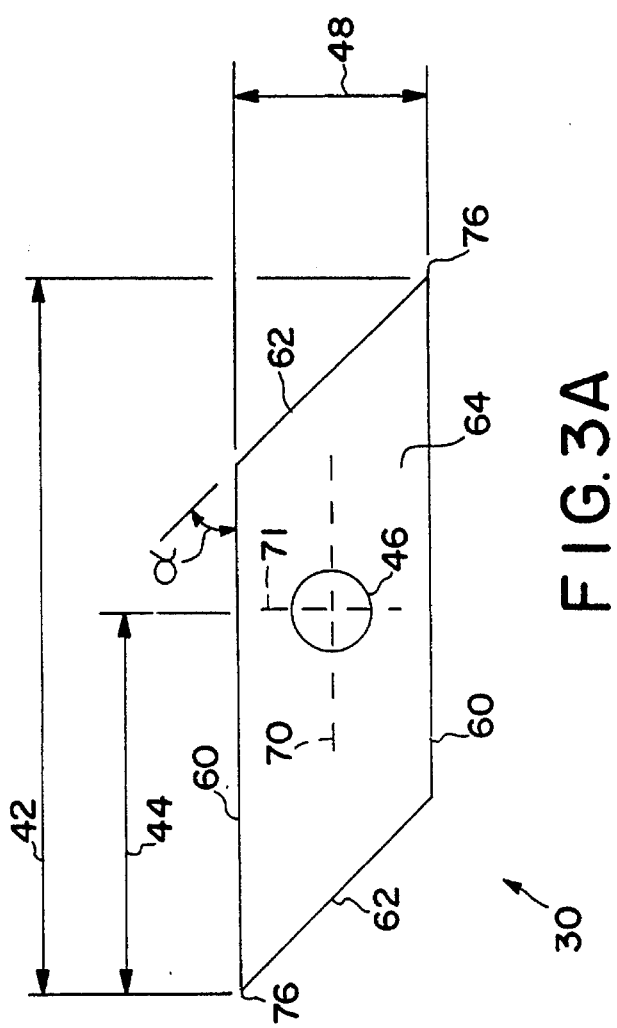
FIG. 3A is a side elevation view of the attachment device shown in FIGS. 2A–2C.

Referring now to FIG. 3A, anchor 30 suitably comprises an elongated member 64, respective top and bottom sections 60, and respective end faces 62. In a preferred exemplary embodiment of the present invention, respective end faces 62 are suitably inclined with respect to a longitudinal axis 70 of the device, for example at angle $\alpha$. In the illustrated embodiment, angle $\alpha$ is suitably on the order of 20 to 75 degrees, and preferably on the order of 30 to 60 degrees, and most preferably about 45 degrees.

Device 30 further comprises a hole 46 extending therethrough. In accordance with one aspect of the present invention, the edges of hole 46 may suitably be radiused and/or bevelled to reduce the likelihood that the edges of hole 46 will cut into sutures 32 (not shown in FIG. 3; see FIG. 2). Although hole 46 is illustrated in FIG. 3 as having a circular cross-section, hole 46 may exhibit any convenient configuration and cross-section, for example an ellipse or an irregular profile.

The diameter of hole 46 is suitably selected to accommodate one or more sutures 32 of conventional size. In a preferred embodiment, the diameter of hole 46 is suitably on the order of 0.020 to 0.080 inches, and preferably about 0.060 inches.

With continued reference to FIG. 3A, the physical dimensions of device 30 may be conveniently selected so that the device may be used in a variety of bone applications. In this regard, although device 30 is described herein in the context of long bone 10, it will be appreciated that device 30 may be employed in the context of any suitable bone wherein it is desired to insert device 30 into a bore formed in the bone mass to thereby substantially imbed the device within the bone.

With continued reference to FIG. 3A, device 30 suitably exhibits a total length 42 on the order of 0.25 to 1.25 inches, and preferably about 0.5 to 0.8 inches, and most preferably about 0.71 inches. In the illustrated embodiment, anchor 30 exhibits a height 48 on the order of 0.08 to 0.15 inches, and preferably about 0.10 to 0.14 inches, and most preferably about 0.12 to 0.125 inches.

In a first preferred embodiment, hole 46 is suitably centered on longitudinal axis 70, midway between respective points 76. In the illustrated embodiment, hole 46 is suitably centered a distance 44 from each of respective corners 76. In a preferred embodiment, dimension 44 is suitably on the order of one-half the length of dimension 42, and preferably about 0.355 inches.

Referring now to FIGS. 3A and 3B, device 30 suitably comprises respective channels or grooves 54 extending along the length thereof. In a particularly preferred embodiment, respective grooves 54 suitably exhibit a radius 50 on the order of 0.010 to 0.080 inches, and preferably about 0.060 inches. Respective channels 54 are suitably configured such that respective sutures 32 (not shown on FIG. 3; see FIG. 2) may conveniently extend along the length of the device during insertion into a bone, thereby permitting the diameter of bore 24 (see FIG. 2) to be only large enough to permit anchor 30 and sutures 32 to be inserted therethrough. That is, the diameter of bore 24 need only be slightly larger than height 48 of device 30 to permit convenient insertion of the anchor/suture combination into the medullary cavity.

With continued reference to FIGS. 2 and 3, device 30 is suitably symmetric about longitudinal axis 70, as well as being suitably symmetric about a transverse axis 71. In this way, device 30 may be inserted into bore 24 without regard to the end-to-end orientation of the device during insertion. In contradistinction to the Noblitt et al. anchor discussed supra, which must be inserted with a particular end of the device corresponding to the leading edge in order to facilitate rotation of the device within the medullary canal, device 30 may be inserted with either end thereof as the leading edge while nonetheless effecting proper rotation of device 30 as shown by arrow 34 in FIG. 2B. More particularly, either one of respective angled faces 62 of device 30 will encounter resistance by matter 20 as the device is urged through bore 24, causing anchor 30 to rotate in the direction indicated by arrow 34. Once the proximal corner 76 of the device is urged past undersurface 17 (i.e., to the left of undersurface 17 in FIG. 2B), the pulling of sutures 32 will result in further rotation of anchor 30 in the direction of arrow 34 in view of the resistance encountered by the trailing end 62 by matter 20. The symmetrical configuration of device 30, which permits rotation of the device in the direction of arrow 34 regardless of which end is inserted into bore 24 as the leading edge, constitutes a significant and time saving advantage of anchor 30 over prior art devices.

With continued reference to FIG. 3B, device 30 suitably exhibits a width dimension 52 on the order of 0.04 to 0.125 inches, and preferably on the order of 0.08 to 0.09 inches, and most preferably about 0.085 inches.

With continued reference to FIG. 3B, respective channels 54 are suitably bounded by respective rails 66. In the illustrated embodiment, respective rails 66 and respective top faces 60 suitably comprise smooth, rounded surfaces. In the alternative embodiment shown in FIG. 3C, anchor 30 may suitably exhibit surface geometries in the form of serrations, ridges, or other formations configured to enhance the frictional engagement between anchor 30 and undersurface 17 as tension is applied to sutures 32 (see FIG. 2C). More particularly, rails 66 may suitably comprise serration 66A and top faces 60 may suitably comprise serrations 60A, as desired.

In accordance with the preferred embodiment of the present invention, anchor 30 may be made from any desirable biocompatible material which exhibits sufficient strength to permit substantial tension to be applied to sutures 32. In a preferred embodiment, anchor 30 may be suitably made from titanium alloy, stainless steel, class 6 implant grade plastic, or PTFE. In an alternate embodiment, and particularly in view of the fact that anchor 30 typically remains in situ permanently once it is installed, the device may be made from a biocompatible material designed to dissolve within the bone after a predetermined period of time, for example, on the order of twelve (12) to fifty-two (52) weeks. If it is desired to construct anchor 30 from a degradable material, device 30 may suitably be made from polyglycolic acid, for example a material distributed by Johnson & Johnson under the name ORTHOSORB™.

Although the subject invention has been described herein in conjunction with the appended drawing figures, those skilled in the art will appreciate that the scope of the invention is not so limited. Various modifications in the arrangement of the components discussed and the steps described herein for using the subject device may be made without departing from the spirit and scope of the invention as set forth in the appended claims.

I claim:

1. A device for attaching soft tissue to bone, comprising:

an elongated anchor having a longitudinal axis;

a bore extending through said anchor and having an axial centerline disposed transversely with respect to and substantially intersecting said longitudinal axis, said bore being configured to receive a suture journaled therethrough; and respective first and second substantially flat, angled end portions oppositely disposed about said bore, said angled end portions being substantially parallel to each other, said bore being disposed along said longitudinal axis approximately midway between said first and second end portions.

2. The device of claim 1, further comprising respective first and second oppositely disposed channels extending along the length of said anchor between said first and second end portions, said channels being configured to receive a portion of said suture therewithin during insertion of said anchor into a bone.

3. The device of claim 1, wherein said first and second end portions lie in respective first and second planes, each of which is substantially parallel to said axial centerline of said bore.

4. The device of claim 1, wherein said axial centerline of said bore intersects said anchor longitudinal axis orthogonally.

5. The device of claim 1, wherein said axial centerline of said bore bisects said anchor longitudinal axis.

6. The device of claim 1, further comprising a channel extending along at least a portion of the length of said anchor between said first and second end portions, said channel being configured to receive said suture therewithin during insertion of said anchor into a medullary canal.

7. The device of claim 6, further comprising respective rails extending along at least a portion of said anchor, such that said channel is disposed between said rails.

8. The device of claim 7, wherein said rails exhibit a smooth, rounded surface configuration.

9. The device of claim 7, wherein said rails exhibit an irregular surface geometry.

10. The device of claim 9, wherein said surface geometry of said rails comprises at least one of serrations and ridges.

11. The device of claim 1, further comprising respective top and bottom portions extending along the length of said anchor between said first and second end portions, wherein said top and bottom portions comprise smooth, rounded surfaces.

12. The device of claim 11, wherein at least one of said top and bottom portions exhibits at least one of ridges and serrations.

13. The device of claim 1, wherein said anchor exhibits a total length in the range of 0.25 to 1.25 inches, and a height in the range of 0.08 to 0.15 inches.

14. The device of claim 13, wherein said bore comprises a circular cross section having a diameter in the range of 0.02 to 0.08 inches.

15. The device of claim 1, wherein said first and second end portions exhibit an angle with respect to said longitudinal axis in the range of 20° to 75°.

16. A medullary suture anchor comprising:

an elongated body having a longitudinal axis associated therewith;

oppositely disposed top and bottom surfaces extending along the length of said body, said top and bottom surfaces being substantially parallel to each other;

first and second oppositely disposed side surfaces extending along the length of said body, each of said first and second side surfaces being bounded by said top and bottom surfaces; and a bore extending through said body, from said first side to said second side, for journaled receipt of a suture, said bore having an axial centerline transverse to said longitudinal axis;

wherein said first side comprises a groove extending along at least a portion of the length of said anchor, said groove being configured to receive said suture therewithin during insertion of said anchor into a medullary canal.

17. The anchor of claim 16, wherein said axial centerline of said bore intersects said longitudinal axis.

18. The anchor of claim 16, wherein said bore is beveled.

19. The anchor of claim 16, wherein said axial centerline of said bore is orthogonal to said longitudinal axis.

20. A medullary suture anchor comprising:

an elongated body having a longitudinal axis associated therewith;

oppositely disposed top and bottom surfaces extending along the length of said body, said top and bottom surfaces being substantially parallel to each other;

first and second oppositely disposed side surfaces extending along the length of said body, each of said first and second side surfaces being bounded by said top and bottom surfaces;

a bore extending through said body for journaled receipt of a suture, said bore having an axial centerline transverse to said longitudinal axis; and respective oppositely disposed flat end portions, each of which is bounded by said first and second side surfaces and said top and bottom surfaces, each of said end portions being disposed in a respective plane which exhibits an angle with respect to said longitudinal axis in the range of 20° to 75°;

wherein said first side comprises a groove extending along at least a portion of the length of said anchor said groove being configured to receive said suture therewithin during insertion of said anchor into a medullary canal.

* * * * *